United States Patent
Umbach et al.

(10) Patent No.: US 7,237,438 B1
(45) Date of Patent: Jul. 3, 2007

(54) SYSTEMS AND METHODS FOR DETERMINING THE VELOCITY OF ULTRASONIC SURFACE SKIMMING LONGITUDINAL WAVES ON VARIOUS MATERIALS

(75) Inventors: Jeffrey A. Umbach, Palm Beach Gardens, FL (US); Kevin D. Smith, Glastonbury, CT (US); R. Bruce Thompson, Ames, IA (US)

(73) Assignee: United Technologies Corporation, Hartford, CT (US)

( * ) Notice: Subject to any disclaimer, the term of this patent is extended or adjusted under 35 U.S.C. 154(b) by 99 days.

(21) Appl. No.: 11/081,922

(22) Filed: Mar. 16, 2005

(51) Int. Cl.
*G01N 29/024* (2006.01)

(52) U.S. Cl. .............................. 73/597; 73/602; 73/628

(58) Field of Classification Search .................. 73/597, 73/598, 600, 602, 606, 620, 627, 628, 632, 73/644; 310/336, 337, 334
See application file for complete search history.

(56) References Cited

U.S. PATENT DOCUMENTS

| 4,406,167 | A | * | 9/1983 | Maeda ......................... 73/622 |
| 4,412,345 | A | | 10/1983 | Workman et al. |
| 4,747,684 | A | | 5/1988 | Weiser |
| 4,788,702 | A | | 11/1988 | Howe et al. |
| 4,862,488 | A | | 8/1989 | Schiller |
| 4,890,496 | A | * | 1/1990 | Birring et al. ................. 73/597 |
| 5,251,486 | A | * | 10/1993 | Thompson et al. ............ 73/597 |
| 5,459,001 | A | * | 10/1995 | Estes et al. ...................... 430/5 |
| 5,631,424 | A | | 5/1997 | Nieters et al. |
| 5,760,522 | A | * | 6/1998 | Kobayashi et al. ...... 310/313 A |
| 5,768,335 | A | | 6/1998 | Shahid |
| 5,922,961 | A | * | 7/1999 | Hsu et al. ...................... 73/606 |
| 6,037,699 | A | * | 3/2000 | Kobayashi et al. ...... 310/313 A |
| 6,112,595 | A | * | 9/2000 | Stanke et al. .................. 73/597 |
| 6,198,796 | B1 | | 3/2001 | Yokoyama et al. |
| 6,332,361 | B1 | * | 12/2001 | Yamada et al. ............... 73/627 |
| 6,424,922 | B1 | | 7/2002 | Bray |
| 6,439,054 | B1 | * | 8/2002 | Gore et al. .................... 73/620 |
| 6,450,036 | B1 | * | 9/2002 | Ashida et al. ................. 73/584 |
| 6,462,340 | B1 | | 10/2002 | Inokuti |
| 6,477,473 | B2 | | 11/2002 | Bray |
| 6,523,418 | B2 | | 2/2003 | Bray |
| 2002/0078759 | A1 | | 6/2002 | Bray |

OTHER PUBLICATIONS

Bescond, C. et al., *Laser-Generated Surface Skimming Longitudinal Wave Measurement of Residual Stress in Shot Peened Samples*, American Institute of Physics Conference Proceedings, vol. 820, Mar. 6, 2006, pp. 1426-1433.
Kielczynski, P. J. et al., *Characterization of Texture in Hexagonal Materials Using a Line of Focus Acoustic Microscope*, IEEE Ultrasonics Symposium Proceedings, Dec. 8, 1991, pp. 1009-1013.
Satish, Shamachary et al. Development of a Scan System for Rayleigh, Shear and Longitudinal Wave Velocity Mapping, IEEE Ultrasonics Symposium Proceedings, vol. 1, Oct. 17, 1999, pp. 597-600.
European Search Report dated Aug. 11, 2006.

\* cited by examiner

*Primary Examiner*—Hezron Williams
*Assistant Examiner*—Jacques M. Saint-Surin
(74) *Attorney, Agent, or Firm*—Tracey R. Loughlin

(57) ABSTRACT

Systems and methods for determining the velocity of ultrasonic surface skimming longitudinal waves on various materials are described herein. In embodiments, a surface skimming longitudinal wave is generated at a first location on a material, at least a portion of that wave is detected at a second location on the material, the time-of-flight of that wave between the first and second locations is determined, and then the velocity of that wave is determined. One or more crystallographic orientations of the material may then be determined based upon that velocity.

16 Claims, 2 Drawing Sheets

FIG.1
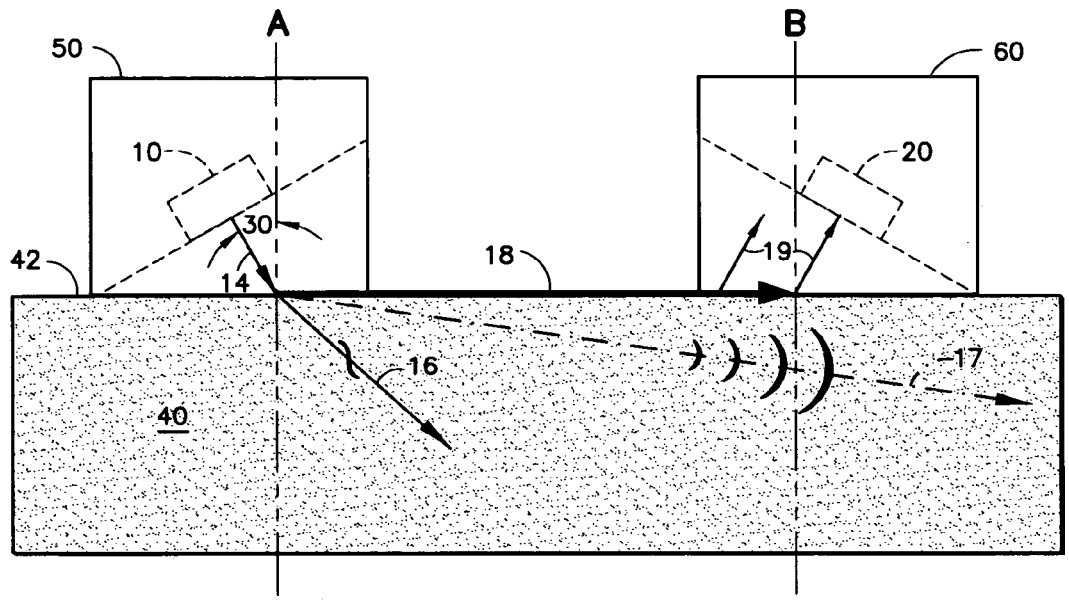
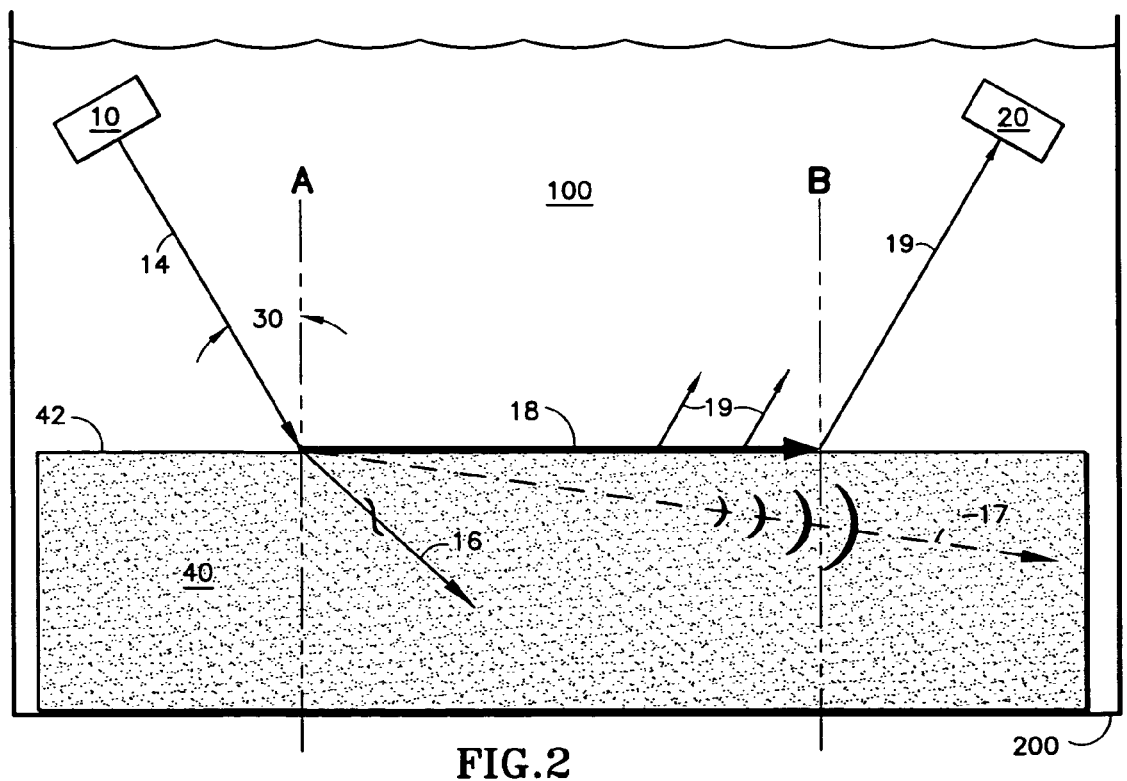
FIG.2

SYSTEMS AND METHODS FOR DETERMINING THE VELOCITY OF ULTRASONIC SURFACE SKIMMING LONGITUDINAL WAVES ON VARIOUS MATERIALS

FIELD OF THE INVENTION

The present invention relates generally to non-destructive measuring techniques, and more specifically, to determining the velocity of ultrasonic surface skimming longitudinal waves on various materials and/or to determining the crystallographic orientations of various materials based upon the velocity of the ultrasonic surface skimming longitudinal waves thereon.

BACKGROUND OF THE INVENTION

Recently, cracks in some gas turbine engine components were attributed to the directionally solidified grains therein having a primary crystal grain orientation that deviated from the [001] axis much further than expected. Therefore, there has become a need to be able to non-destructively determine the primary crystal grain orientation in directionally solidified and single crystal materials to ensure that the primary crystal grain orientation falls within certain limits of a predetermined crystal axis.

One conventional non-destructive method of determining the crystallographic orientations of single crystal materials, commonly known as the Laue method, involves directing x-rays onto the material, where they are reflected therefrom and/or therethrough and captured as an x-ray diffraction pattern, which can then be analyzed to determine the crystallographic orientations of the material. The Laue method, while capable of determining both the primary and secondary grain orientations of single crystal materials, is time consuming and cannot be easily utilized to determine the crystallographic orientations of various gas turbine engine components on-wing or in production environments, etc. Furthermore, the Laue method cannot be feasibly used on columnar-grained materials (i.e., directionally solidified materials) because it would be too expensive and too cumbersome to reorient the material with respect to the stacking axis to determine the crystallographic orientations of each individual grain therein.

Therefore, it would be desirable to have improved systems and methods for accurately and non-destructively determining the crystallographic orientations of directionally solidified and/or single crystal materials. It would be desirable if the crystallographic orientations of such materials could be determined based upon the measured velocity of ultrasonic surface skimming longitudinal waves thereon. It would also be desirable if such systems and methods could be easily used in various environments (i.e., on-wing, in production environments, in engine overhaul shops, etc.). It would be even further desirable if these velocity determining systems and methods could be used for other purposes, such as for sorting various materials, etc.

SUMMARY OF THE INVENTION

The above-identified shortcomings of existing systems and methods for determining the crystallographic orientations of a material are overcome by embodiments of the present invention, which relates to systems and methods for non-destructively measuring the velocity of ultrasonic surface skimming longitudinal waves on a material. The measured velocity can then be used for various purposes, such as for determining the crystallographic orientations of the material, sorting various materials, etc.

Embodiments of this invention comprise methods for determining the velocity of an ultrasonic surface skimming longitudinal wave on a material. These methods may comprise: generating an ultrasonic surface skimming longitudinal wave at a first location on the material; detecting at least a portion of the ultrasonic surface skimming longitudinal wave at a second location on the material; and determining the velocity of the ultrasonic surface skimming longitudinal wave between the first location and the second location. Once the velocity is determined, the method may further comprise: determining at least one crystallographic orientation of the material based upon the velocity; sorting a plurality of materials from one another based upon the velocity; etc.

Embodiments of this invention also comprise methods for determining one or more crystallographic orientations of a material. These methods may comprise: generating an ultrasonic wave at a first location on the material; detecting at least a portion of the ultrasonic wave at a second location on the material; determining at least one crystallographic orientation of the material from the detected ultrasonic wave. The determining step may comprise: measuring the time of flight of the ultrasonic wave; determining the longitudinal velocity of the material based upon the distance between the first location and the second location and the time of flight of the ultrasonic wave; and determining at least one crystallographic orientation of the material utilizing the longitudinal velocity of the material. These ultrasonic waves may comprise surface skimming longitudinal waves having a longitudinal velocity that is dependent upon the primary crystallographic orientation of the material, but not upon the secondary crystallographic orientation of the material.

Embodiments of this invention comprise systems for measuring the velocity of an ultrasonic surface skimming longitudinal wave on a material. These systems may comprise: an ultrasonic wave emitter; an ultrasonic wave detector; and means for determining the velocity of an ultrasonic surface skimming longitudinal wave on the material. The systems may further comprise means for determining at least one crystallographic orientation of the material utilizing the velocity of the ultrasonic surface skimming longitudinal wave. The ultrasonic wave emitter should be capable of emitting ultrasonic waves at a predetermined angle with respect to the surface of the material. The ultrasonic wave detector should be capable of detecting at least a portion of the ultrasonic surface skimming longitudinal wave at a predetermined location.

Embodiments of this invention may be utilized on directionally solidified materials, single crystal materials, and/or polycrystalline materials. These materials may comprises various gas turbine engine components, such as, but not limited to, turbine blades, combustor liners, blade outer air seals, etc.

Embodiments of this invention may be utilized in various environments, such as, but not limited to, (a) while the component is on-wing; (b) while the component is in a production environment; (c) while the component is in an engine overhaul facility; (d) while the component is in a material salvage facility; and/or (e) while the component is in a re-work facility.

The systems and methods of this invention may utilize contact configurations, immersion configurations, and/or bubbler configurations.

Further details of this invention will be apparent to those skilled in the art during the course of the following description.

DESCRIPTION OF THE DRAWINGS

Embodiments of this invention are described herein with reference to various figures, wherein like characters of reference designate like parts throughout the drawings, in which:

FIG. 1 is a schematic drawing showing an embodiment of this invention utilizing a contact technique having a pitch-catch ultrasonic wave configuration;

FIG. 2 is a schematic drawing showing an embodiment of this invention utilizing an immersion technique having a pitch-catch ultrasonic wave configuration.

DETAILED DESCRIPTION OF THE INVENTION

Figure 3:
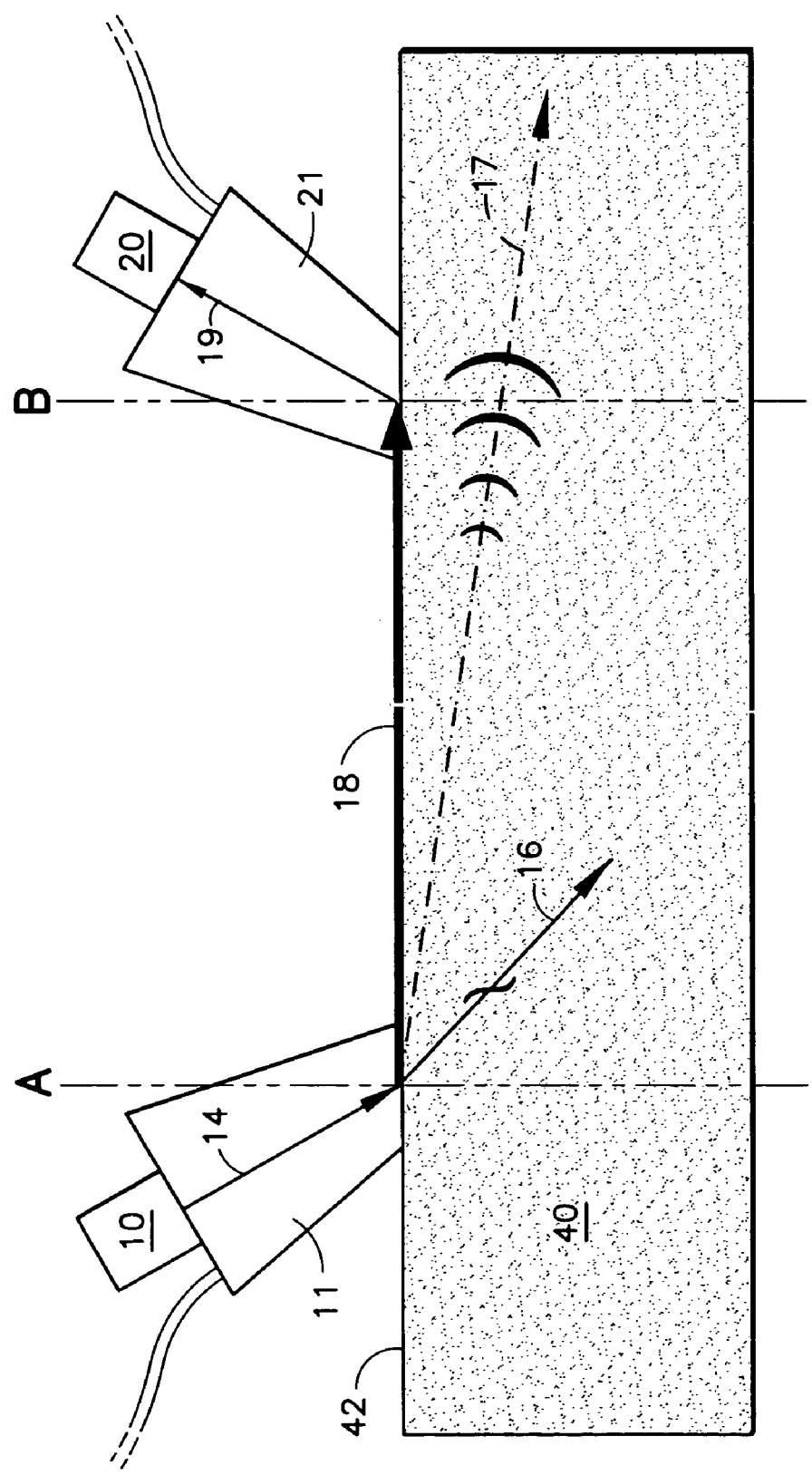
FIG. 3 is a schematic drawing showing an embodiment of this invention utilizing a bubbler technique having a pitch-catch ultrasonic wave configuration.

For the purposes of promoting an understanding of the invention, reference will now be made to some embodiments of this invention as illustrated in FIGS. 1-3 and specific language used to describe the same. The terminology used herein is for the purpose of description, not limitation. Specific structural and functional details disclosed herein are not to be interpreted as limiting, but merely as a basis for teaching one skilled in the art to variously employ the present invention. Any modifications or variations in the depicted structures and methods, and such further applications of the principles of the invention as illustrated herein, as would normally occur to one skilled in the art, are considered to be within the spirit and scope of this invention as described and claimed.

This invention relates to systems and methods for measuring the velocity of ultrasonic surface skimming longitudinal waves on various materials. Embodiments of these systems and methods may be used for non-destructively determining at least one crystal grain orientation (i.e., primary and/or secondary, etc.) of various materials based upon the measured velocity of the ultrasonic surface skimming longitudinal waves thereon. Such embodiments may be utilized on any single grain of material (i.e., on columnar grains in directionally solidified materials, on single grains in single crystal materials, and/or on single grains in polycrystalline materials), provided the grain is large enough to allow the emitter and the detector to be properly positioned with respect thereto. Embodiments of this invention may also be used for other purposes, such as, for example, for sorting various materials, for any purposes where only one surface of a material is available for evaluation, and/or for any purposes where longitudinal velocity measurements may be useful, etc. The systems of this invention may be small and compact enough to be used almost anywhere in various environments, such as in production environments, on-wing, in engine overhaul facilities, in material salvage or re-work facilities, etc.

Embodiments of this invention utilize a contact technique having a pitch-catch ultrasonic wave configuration as shown in FIG. 1. An emitter 10 positioned within a contact transducer 50 at a predetermined angle 30 generates ultrasonic shear waves 16 and ultrasonic compressional waves 17 in the material 40. When the compressional waves 17 are refracted at angles that include waves propagating along the surface 42 of the material 40, a surface skimming longitudinal wave 18 is created. Generally, this means that the incident wave 14 should be near the first critical angle as defined by Snell's law for the wedge material of the contact transducers 50, 60 and the material 40 be analyzed. The surface skimming longitudinal wave 18 is a leaky wave that emits leaking ultrasonic energy 19 from the surface 42 of the material 40. This leaking ultrasonic energy 19 is transmitted to the detector when the detector 20 is in direct contact with the surface 42 of the material 40. A detector 20 positioned within a contact transducer 60 detects the leaking ultrasonic waves 19, and the time-of-flight of the surface skimming longitudinal waves 18 between points A and B can be determined therefrom. The surface skimming longitudinal waves 18 and the associated leaking ultrasonic waves 19 arrive at the detector 20 first because they travel faster than the shear wave 16 and any of its reflected components. The time-of-flight of the surface skimming longitudinal wave 18 is indicative of the longitudinal velocity of the material 40, which varies depending upon the primary crystal grain orientation of the material.

The emitter 10 may comprise any ultrasonic wave emitter capable of emitting suitable ultrasonic waves. The detector 20 may comprise any ultrasonic wave detector capable of detecting the desired ultrasonic waves. In embodiments, the ultrasonic waves may have a frequency of about 5-15 MHz, but many other suitable frequencies are also possible, and this invention is not limited to any particular frequency range.

In operation, the emitter 10 may be adjusted to emit ultrasonic waves at any suitable angle 30, such as, but not limited to, about 22-28° from normal to the surface 42 of the material 40, so as to create compressional waves 17 at an angle near the longitudinal critical angle of the average velocity of the material 40.

The precise locations of points A and B can be easily determined by utilizing two reference samples having known velocities ($V_1$ and $V_2$, respectively) to calibrate the transducers 50 and 60, which are held at a constant distance from one another. First, the time of flight ($TOF_1$ and $TOF_2$, respectively) of the surface skimming longitudinal waves 18 can be measured on each of the two reference samples. The two unknowns (surface distance between points A and B, SD, and time within the contact transducers 50, 60, TW) can then be determined for the ultrasonic wave. The surface distance, SD, can be determined by the following equation.

$$SD=(TOF_1-TOF_2)*(V_2*V_1)/(V_2-V_1)$$

The time of flight attributable to the time that the ultrasonic wave spends within the contact transducers 50 and 60, TW, can be determined by the following equation.

$$TW=TOF_1-SD/V_1$$

Once the values of SD and TW are known, one can then determine the velocity ($V_{unk}$) of an unknown material by measuring the time of flight ($TOF_{unk}$) of the ultrasonic surface skimming wave thereon and utilizing that $TOF_{unk}$ in the following equation.

$$V_{unk}=SD/(TOF_{unk}-TW)$$

Thereafter, since longitudinal wave velocity variations are primary crystal grain orientation dependent, the primary crystal grain orientation of the material 40 may be determined.

The primary crystal grain orientations of the material 40 may be determined in various ways. In some embodiments, the primary crystal grain orientations of the material 40 may be determined by comparing the measured/calculated longitudinal velocity of the material 40 with samples having known crystal grain orientations and known longitudinal velocities. In other embodiments, the primary crystal grain orientations of the material 40 may be determined from theoretical calculations based on single crystal elastic constants.

The secondary crystal grain orientations of the material 40 may also be determined. This may be accomplished by orienting the contact transducer pair 50, 60 in a direction parallel to the secondary orientation and performing the same calculations as performed for determining the primary orientation. As with the primary orientation, velocity is first deduced from the time of flight measurement, and then the associated orientation may be determined either from the measured or calculated values.

Embodiments of this invention may also utilize an immersion technique having a pitch-catch ultrasonic wave configuration as shown in FIG. 2. The immersion technique may be carried out in a fluid bath 200 in any suitable fluid medium 100, such as, but not limited to, water, oil, etc. The immersion technique is similar to the contact technique described above, except in the immersion technique, there are no contact transducers 50, 60, and instead, a constant fluid path is maintained between the emitter 10 and the detector 20. A constant fluid path is also maintained between the emitter 10 and the surface 42 of the material 40, and between the detector 20 and the surface 42 of the material 40. In immersion embodiments, the leaking ultrasonic energy 19 will be transmitted to the detector 20, and may also be emitted into the fluid medium 100. In the immersion technique, as in the contact technique, the distance between the emitter 10 and the detector 20 is constant, and the emitter 10 and the detector 20 are held in fixed positions, so the distance between points A and B is constant. The calculations and measurements in the immersion technique are otherwise similar to those discussed above for the contact technique.

Embodiments of this invention may also utilize a bubbler technique having a pitch-catch ultrasonic wave configuration as shown in FIG. 3. The bubbler technique is similar to the contact technique described above, but in the bubbler technique, any suitable fluid (i.e., water, oil, etc.) may be used to carry the ultrasonic wave from the emitter 10 to the material 40, and from the material 40 to the detector 20. Tubes or other suitable bubbler transducers 11, 21 may be used to carry fluid to maintain a fluid path between the emitter 10 and the material 40, and between the detector 20 and the material 40. In bubbler embodiments, the leaking ultrasonic energy 19 will be transmitted to the detector 20 through the fluid in the bubbler transducer 21. The calculations and measurements in the bubbler technique are otherwise similar to those discussed above for the contact technique.

This invention can be used to determine the crystallographic orientations of many directionally solidified or single crystal materials, such as those used in aero and/or land based gas turbine engine components. Some exemplary components that this invention may be utilized with include, but are not limited to, high pressure turbine blades, low pressure turbine blades, combustor liners, blade outer air seals, etc.

This invention can be used for various purposes. In addition to using the velocity of the surface skimming longitudinal waves 18 to determine the crystal grain orientations of various materials, the velocity of the surface skimming longitudinal waves 18 may also be used for other purposes, such as, for example, to sort various materials from one another, to determine a longitudinal velocity that could then be used for a thickness measurement, etc. Various materials may be sorted from one another because different materials would have different velocities.

Various contact, immersion and bubbler techniques were utilized to verify the feasibility and accuracy of this invention. Ultrasonic surface skimming longitudinal waves were observed and measured for various polycrystalline, directionally solidified and single crystal materials, including various nickel alloys, titanium alloys, aluminum alloys and copper alloys.

In embodiments, the contact technique utilized wedges made of Perspex® material having 5-15 MHz transducers embedded therein. The incident angles 30 tested varied from about 25-30° from normal to the surface 42 of the material 40. Several samples comprised single crystal materials so the velocity dependence upon primary crystal grain orientation could be tested. Bulk longitudinal velocities of various materials were also measured at specific orientations so comparisons thereof could be made with the velocities of the surface skimming longitudinal waves.

In embodiments, the immersion technique utilized 10 MHz transducers and water. Several measurements were made on various materials having known velocities. Some embodiments utilized a single transducer in pulse/echo mode, and measurements of time-of-flight for a reflected signal from an edge were obtained. Other embodiments utilized two immersion transducers in a pitch/catch configuration in a fixture having a known separation therebetween, and measurements of time-of-flight for an ultrasonic surface skimming longitudinal wave were obtained.

In embodiments, the bubbler technique utilized a fixture that held small bubbler transducers 11, 21 at fixed positions, and measurements of time-of-flight for an ultrasonic surface skimming longitudinal wave were obtained.

The velocities of the ultrasonic surface skimming longitudinal waves of samples having unknown crystal grain orientations were compared to velocities of samples having known crystal grain orientations, which had their crystal grain orientations previously determined via the Laue x-ray technique. Such velocities were measured on unknown samples at various positions and orientations on the surfaces thereof (i.e., throughout 360°), and crystal grain orientations were determined therefrom. The crystal grain orientations obtained by the methods of this invention were found to match those obtained by the Laue technique within about +/−1°.

While ultrasonic waves (i.e., longitudinal waves and shear waves) have been used to inspect for subsurface reflectors in polycrystalline materials, and ultrasonic waves (i.e., Rayleigh surface waves) have been used to measure/inspect for surface anomalies in various polycrystalline materials, ultrasonic waves (i.e., surface skimming longitudinal waves) have not been used to determine velocities of various materials to determine crystal grain orientations of directionally solidified or single crystal materials and/or to sort various materials, etc. When ultrasonic longitudinal and shear waves are used to inspect for subsurface reflectors in polycrystalline materials, the amplitude and time-of-flight of reflected ultrasonic waves can be used to detect and evaluate features within the volume of a material. When ultrasonic Rayleigh surface waves are used to measure/inspect for surface anomalies in various polycrystalline materials, the anomalies in the Rayleigh surface waves can be used to evaluate surface defects on a material. When ultrasonic surface skimming longitudinal waves are used, the velocity at which an ultrasonic surface skimming longitudinal wave travels along the surface of a material can be used to determine the crystal grain orientations of the material, among other things. These are three very different techniques, which measure very different items of interest on different types of materials.

As described above, this invention provides systems and methods for non-destructively determining the velocity of surface skimming longitudinal waves on various materials. Advantageously, the systems and methods of this invention can be easily and economically used in various environments (i.e., on-wing, in production environments, in engine overhaul facilities, in material salvage facilities, in re-work facilities, etc.). Furthermore, the systems and methods of this invention can be used for various purposes (i.e., to determine crystal grain orientations of various materials, to sort various materials, for any purposes where longitudinal velocity measurements may be useful, etc.). In addition to being able to use the systems and methods of this invention in environments where the Laue technique cannot be used, this invention could also be used instead of, and much easier than, the Laue technique in many instances. Many other advantages will be apparent to those skilled in the relevant art.

Various embodiments of this invention have been described in fulfillment of the various needs that the invention meets. These embodiments are merely illustrative of the principles of various embodiments of the present invention. Numerous modifications and adaptations thereof will be apparent to those skilled in the art without departing from the spirit and scope of the present invention. Thus, it is intended that the present invention cover all suitable modifications and variations as come within the scope of the appended claims and their equivalents.

What is claimed is:

1. A method of determining the crystallographic orientation of a material from the velocity of an ultrasonic surface skimming longitudinal wave on the material, comprising:
   generating an ultrasonic surface skimming longitudinal wave at a first location on the material;
   detecting at least a portion of the ultrasonic surface skimming longitudinal wave at a second location on the material;
   determining the velocity of the ultrasonic surface skimming longitudinal wave between the first location and the second location;
   determining at least the primary crystal grain orientation of the material from the velocity; and
   determining if the primary crystal grain orientation of the material falls within predetermined limits of a predetermined crystal axis.

2. The method of claim 1, wherein the method comprises at least one of the following: a contact technique, an immersion technique, and a bubbler technique.

3. The method of claim 1, wherein the method further comprises:
   sorting a plurality of materials from one another based upon at least one of the velocity and the primary crystal orientation of the material.

4. A method of determining at least one crystallographic orientation of a material, comprising:
   generating an ultrasonic wave at a first location on the material;
   detecting at least a portion of the ultrasonic wave at a second location on the material;
   determining at least one crystallographic orientation of the material from the detected ultrasonic wave; and
   determining of the at least one crystallographic orientation of the material falls within predetermined limits of at least one predetermined crystal axis.

5. The method of claim 4, wherein the determining step comprises:
   measuring the time of flight of the ultrasonic wave;
   determining the longitudinal velocity of the material based upon the distance between the first location and the second location and the time of flight of the ultrasonic wave; and
   determining at least one crystallographic orientation of the material utilizing the longitudinal velocity of the material.

6. The method of claim 4, wherein the ultrasonic wave comprises a surface skimming longitudinal wave having a longitudinal velocity that is dependent upon the primary crystallographic orientation of the material, but not upon the secondary crystallographic orientation of the material.

7. The method of claim 4, wherein the material comprises at least one of: a directionally solidified material, a single crystal material, and a polycrystalline material.

8. The method of claim 4, wherein the material comprises a gas turbine engine component.

9. The method of claim 8, wherein the gas turbine engine component comprises at least one of: a turbine blade, a combustor liner, and a blade outer air seal.

10. The method of claim 4, wherein the method is utilized via at least one of: (a) while the component is on-wing; (b) while the component is in a production environment; (c) while the component is in an engine overhaul facility; (d) while the component is in a material salvage facility; and (e) while the component is in a re-work facility.

11. The method of claim 4, wherein the at least one crystallographic orientation is determined via at least one of: a contact technique, an immersion technique, and a bubbler technique.

12. A system for determining the crystallographic orientation of a material by measuring the velocity of an ultrasonic surface skimming longitudinal wave on the material, comprising:
   an ultrasonic wave emitter;
   an ultrasonic wave detector;
   means for determining the velocity of an ultrasonic surface skimming longitudinal wave on the material;
   means for determining at least one crystallographic orientation of the material from the velocity; and
   means for determining if the at least one crystallographic orientation of the material falls within predetermined limits of at least one predetermined crystal axis.

13. The system of claim 12, wherein the ultrasonic wave emitter is capable of emitting ultrasonic waves at a predetermined angle with respect to the surface of the material.

14. The system of claim 12, wherein the ultrasonic wave detector is capable of detecting at least a portion of the ultrasonic surface skimming longitudinal wave at a predetermined location.

15. The system of claim 12, wherein the apparatus comprises at least one of: a contact configuration, an immersion configuration, and a bubbler configuration.

16. A method for determining at least one crystal orientation of a material, comprising:
   providing the system of claim 12; and
   determining at least one crystal orientation of the material using the system.

* * * * *